United States Patent
Schrattenholz

(10) Patent No.: US 8,012,697 B2
(45) Date of Patent: Sep. 6, 2011

(54) MONOCLONAL ANTI-ANNEXIN A3 ANTIBODIES FOR THE DETECTION OF PROSTATE CARCINOMA

(75) Inventor: Andre Schrattenholz, Mainz (DE)

(73) Assignee: ProteoSys AG, Mainz (DE)

( * ) Notice: Subject to any disclaimer, the term of this patent is extended or adjusted under 35 U.S.C. 154(b) by 176 days.

(21) Appl. No.: 12/303,825

(22) PCT Filed: Jun. 11, 2007

(86) PCT No.: PCT/EP2007/005134
§ 371 (c)(1),
(2), (4) Date: Dec. 8, 2008

(87) PCT Pub. No.: WO2007/141043
PCT Pub. Date: Dec. 13, 2007

(65) Prior Publication Data
US 2010/0233160 A1    Sep. 16, 2010

Related U.S. Application Data

(60) Provisional application No. 60/812,089, filed on Jun. 9, 2006, provisional application No. 60/859,489, filed on Nov. 17, 2006.

(51) Int. Cl.
G01N 33/53 (2006.01)
G01N 33/574 (2006.01)
C07K 16/00 (2006.01)
C12P 21/08 (2006.01)

(52) U.S. Cl. ...... 435/7.1; 435/721; 435/723; 530/387.1; 530/387.7; 530/387.9; 530/388.1; 530/389.7

(58) Field of Classification Search ............. None
See application file for complete search history.

(56) References Cited

U.S. PATENT DOCUMENTS

| | | | |
|---|---|---|---|
| 7,732,148 B2 * | 6/2010 | Cahill et al. | 435/7.1 |
| 2007/0172900 A1 * | 7/2007 | Cahill et al. | 435/7.23 |
| 2008/0200385 A1 * | 8/2008 | Cahill et al. | 514/12 |

FOREIGN PATENT DOCUMENTS

| | | |
|---|---|---|
| EP | 1 724 586 A | 11/2006 |
| WO | 03/009814 A | 2/2003 |
| WO | 2005/078124 A | 8/2005 |
| WO | WO 2006/125580 A1 * | 11/2006 |

OTHER PUBLICATIONS

Taber's Cyclopedic Medical Dictionary (1985, F.A. Davis Company, Philadelphia, p. 274).*
Busken, C et al. (Digestive Disease Week Abstracts and Itinerary Planner, 2003, abstract No: 850).*
Kaiser (Science, 2006, 313: 1370).*
Krontiris and Capizzi (Internal Medicine, 4th Edition, Editor-in-chief Jay Stein, Elsevier Science, 1994 Chapters 71-72, pp. 699-729).*
Tanaka et al. (1985 Proc. Natl. Acad. Sci USA 82:3400-3404.*
Harlow and Lane (Antibodies, a Laboratory Manual, Cold Spring Harbor Laboratory Press, 1988, p. 141-142).*
Diakonova et al., "Localization of five annexins in J774 macrophages and on isolated phagosomes", J Cell Sci, vol. 110, (PT 10), May 1997, pp. 1199-1213.
Ernst et al: Purification and characterization of an abundant cytosolic protein from human neutrophils that promotes Ca2(+)-dependent aggregation of isolated specific granules. J Clin Invest, vol. 85, No. 4, Apr. 1990, pp. 1065-1071.
Le Cabec et al: "Differential expression of two forms of annexin 3 in human neutrophils and monocytes and along their differentiation", Biochem Biophys Res Commun, vol. 189, No. 3, Dec. 30, 1992, pp. 1471-1476.
Madoz-Gurpide J. et al: "Proteomics-based validation of genomic data: applications in colorectal cancer diagnosis" Mol Cell Proteomics, vol. 5, No. 8, May 29, 2006, pp. 1471-1483.

* cited by examiner

Primary Examiner — Peter J Reddig
(74) Attorney, Agent, or Firm — Rothwell, Figg, Ernst & Manbeck, P.C.

(57) ABSTRACT

The present invention relates to a method for the diagnosis of prostate carcinoma comprising the determination of annexin A3, particularly of extracellular annexin A3 with highly specific antibodies, particularly with monoclonal antibodies. The present invention further refers to a test reagent comprising such antibodies.

18 Claims, 14 Drawing Sheets

— anti-rabbit 1:50
— control serum (rabbit) 1:500
— Petros 1:500 (Wozny et al, 2006)

___ anti-mouse 1:50
___ control antibody (mouse) 1:1

___ anti-mouse 1:50
___ tgc7ProVII5C5 5µg/ml

___ anti-mouse 1:50
___ tgc7ProVII5C5 20µg/ml

SEQUENCE LISTING

<160> NUMBER OF SEQ ID NOS: 13

<210> SEQ ID NO 1
<211> LENGTH: 12
<212> TYPE: PRT
<213> ORGANISM: Artificial Sequence
<220> FEATURE:
<223> OTHER INFORMATION: antibody
<220> FEATURE:
<221> NAME/KEY: MISC_FEATURE
<222> LOCATION: (1)..(12)

<400> SEQUENCE: 1

```
Val Arg Asp Tyr Pro Asp Phe Ser Pro Ser Val Asp
1               5                   10
```

```
<210> SEQ ID NO 2
<211> LENGTH: 12
<212> TYPE: PRT
<213> ORGANISM: Artificial Sequence
<220> FEATURE:
<223> OTHER INFORMATION: antibody
<220> FEATURE:
<221> NAME/KEY: MISC_FEATURE
<222> LOCATION: (1)..(12)

<400> SEQUENCE: 2

Met Leu Ile Ser Ile Leu Thr Glu Arg Ser Asn Ala
1               5                   10
```

```
<210> SEQ ID NO 3
<211> LENGTH: 28
<212> TYPE: PRT
<213> ORGANISM: Artificial Sequence
<220> FEATURE:
<223> OTHER INFORMATION: antibody
<220> FEATURE:
<221> NAME/KEY: MISC_FEATURE
<222> LOCATION: (1)..(28)

<400> SEQUENCE: 3

Gly Asp Phe Arg Lys Ala Leu Leu Thr Leu Ala Asp Gly Arg Arg Asp
1               5                   10                  15

Glu Ser Leu Lys Val Asp Glu His Leu Ala Lys Gln
            20                  25
```

```
<210> SEQ ID NO 4
<211> LENGTH: 25
<212> TYPE: PRT
<213> ORGANISM: Artificial Sequence
<220> FEATURE:
<223> OTHER INFORMATION: antibody
<220> FEATURE:
<221> NAME/KEY: MISC_FEATURE
<222> LOCATION: (1)..(25)

<400> SEQUENCE: 4

Lys Leu Thr Phe Asp Glu Tyr Arg Asn Ile Ser Gln Lys Asp Ile Val
1               5                   10                  15

Asp Ser Ile Lys Gly Glu Leu Ser Gly
            20                  25
```

```
<210> SEQ ID NO 5
<211> LENGTH: 17
<212> TYPE: PRT
<213> ORGANISM: Artificial Sequence
<220> FEATURE:
<223> OTHER INFORMATION: antibody
<220> FEATURE:
<221> NAME/KEY: MISC_FEATURE
<222> LOCATION: (1)..(17)

<400> SEQUENCE: 5

Ile Met Val Ser Arg Ser Glu Ile Asp Leu Leu Asp Ile Arg Thr Glu
1               5                   10                  15

Phe
```

```
<210> SEQ ID NO 6
<211> LENGTH: 17
<212> TYPE: PRT
<213> ORGANISM: Artificial Sequence
```

```
<220> FEATURE:
<223> OTHER INFORMATION: antibody
<220> FEATURE:
<221> NAME/KEY: MISC_FEATURE
<222> LOCATION: (1)..(17)

<400> SEQUENCE: 6

Tyr Ser Ala Ile Lys Ser Asp Thr Ser Gly Asp Tyr Glu Ile Thr Leu
1               5                   10                  15
Leu

<210> SEQ ID NO 7
<211> LENGTH: 9
<212> TYPE: PRT
<213> ORGANISM: Artificial Sequence
<220> FEATURE:
<223> OTHER INFORMATION: antibody

<400> SEQUENCE: 7

Asp Tyr Pro Asp Phe Ser Pro Ser Val
1               5

<210> SEQ ID NO 8
<211> LENGTH: 9
<212> TYPE: PRT
<213> ORGANISM: Artificial Sequence
<220> FEATURE:
<223> OTHER INFORMATION: antibody

<400> SEQUENCE: 8

Leu Ile Ser Ile Leu Thr Glu Arg Ser
1               5

<210> SEQ ID NO 9
<211> LENGTH: 6
<212> TYPE: PRT
<213> ORGANISM: Artificial Sequence
<220> FEATURE:
<223> OTHER INFORMATION: antibody

<400> SEQUENCE: 9

Phe Arg Lys Ala Leu Leu
1               5

<210> SEQ ID NO 10
<211> LENGTH: 9
<212> TYPE: PRT
<213> ORGANISM: Artificial Sequence
<220> FEATURE:
<223> OTHER INFORMATION: antibody

<400> SEQUENCE: 10

Ser Leu Lys Val Asp Glu His Leu Ala
1               5

<210> SEQ ID NO 11
<211> LENGTH: 9
<212> TYPE: PRT
<213> ORGANISM: Artificial Sequence
<220> FEATURE:
<223> OTHER INFORMATION: antibody

<400> SEQUENCE: 11

Thr Phe Asp Glu Tyr Arg Asn Ile Ser
1               5

<210> SEQ ID NO 12
```

```
<211> LENGTH: 9
<212> TYPE: PRT
<213> ORGANISM: Artificial Sequence
<220> FEATURE:
<223> OTHER INFORMATION: antibody

<400> SEQUENCE: 12

Ser Arg Ser Glu Ile Asp Leu Leu Asp
1               5

<210> SEQ ID NO 13
<211> LENGTH: 13
<212> TYPE: PRT
<213> ORGANISM: Artificial Sequence
<220> FEATURE:
<223> OTHER INFORMATION: antibody

<400> SEQUENCE: 13

Ala Ile Lys Ser Asp Thr Ser Gly Asp Glu Tyr Glu Ile
1               5                   10
```

MONOCLONAL ANTI-ANNEXIN A3 ANTIBODIES FOR THE DETECTION OF PROSTATE CARCINOMA

CROSS REFERENCE TO RELATED APPLICATION

This application is a 35 U.S.C. 371 National Phase Entry Application from PCT/EP2007/005134, filed Jun. 11, 2007, which claims the benefit of Provisional Applications 60/812, 089 filed Jun. 9, 2006 and 60/859,489 filed Nov. 17, 2006 the disclosures of which are incorporated herein by their entirety.

The present invention relates to a method for the diagnosis of prostate carcinoma comprising the determination of annexin A3, particularly of extracellular annexin A3 with highly specific antibodies, particularly with monoclonal antibodies. The present invention further refers to a test reagent comprising such antibodies.

With men, the prostate carcinoma ranks first among malignant incidences and, despite a moderate biological aggressiveness compared with other tumour entities, second among cancer-induced deaths (Greenlee et al., 2000). There are excellent curative options for locally limited stages, namely surgery (Huland, 2001a) and/or radiation therapy (Wiegel, 1998), whereas in the case of advanced stages merely temporarily effective methods of hormone ablation can be used. The newly occurring progress of the initial disease during the hormone ablative therapy, usually after 2-3 years, is referred to as hormone refractory state. At present, there are only palliative therapy options for the hormone refractory prostate carcinoma (Knox & Moore, 2001).

Consequently, it is of crucial importance to diagnose the prostate carcinoma at an early stage. With PSA, the prostate-specific antigen, a highly sensitive serum tumour marker for initial diagnostics (Stamey et al., 1987) and follow-up action (Haese et al., 1999) of the prostate carcinoma is available.

Since PSA is to a large extent organ-specific, but not tumour-specific, benign prostate disease can also be associated with an increase of PSA exceeding the range of 4 ng/ml considered as upper limit. The following invasive production of at least 10 transrectally obtained prostate punch biopsies at present represents the gold standard in definitive diagnostics of prostate carcinoma in this situation (Miller & Weißbach, 1999a,b). Up to 25% of the patients suffer from relevant intricacies, however, which render a further consultation (13% of the patients) and a hospitalisation (about 6% of the affected patients) necessary (Lujan et al., 2001; Djavan et al., 2001). Apart from the risk of an infect of the urinary passage or the risk of prostatitis, haemorrhage and the painfulness of the operation predominate as further undesired occurrences, which is counteracted in few institutions only by carrying out locally anaesthetic measures (Irani et al., 1997; Issa et al., 2000; Alavi et al., 2001). A punch biopsy carried out in the case of about 75% of those patients having PSA values in the range of between 4-10 ng/ml will show negative, that is benign, diagnostic findings (Huland, 2001b). If the indication for carrying out prostate punch biopsies was derived already from PSA values starting from 2.5 ng/ml, as presently suggested by some authors (Djavan et al., 1999; Okihara et al., 2001), this invasive method of physical examination would have to be expected of every fourth man aged between 50 and 75 years (Huland, 2001b).

New markers with enhanced specificity over PSA, including its subforms (Jung et al., 2001; Makinen et al., 2001), are therefore of high interest for the prostate carcinoma diagnostics since they might better define the indications for carrying out invasive punch biopsies and thus might reduce the number of patients having to undergo this examination. A tumour marker suitable also for non-invasively obtained probe material like plasma or exprimate urine with outstanding specificity could thus be the newly characterized annexin A3 (ANXA3) marker (Wozny et al., 2006).

ANXA3 is a rather rare representative of the family of annexins, a class of $Ca^{2+}$ effector proteins which carry out their versatile effects by binding to particular phospholipids. They can form networks on the membrane surface and can thus organise membrane microdomains and recruiting foci for interacting proteins (Gerke et al., 2005).

Annexins thereby play important roles in cell differentiation, cell migration and also in immunomodulation. Apart from membrane structure and membrane transport, there are also membrane- and phospholipid-independent protein-protein-interactions of the annexins (Rescher & Gerke 2004; Gerke & Moss, 2002). Annexins participate as principal components of matrix vesicles in cartilage formation and bone mineralisation (Wang et al., 2003). The differential expression of ANXA3 is particularly interesting with regard to the unusual frequency of occurrence of osteoblastic bone metastases in the case of prostate carcinoma (Keller et al., 2001).

ANXA3 occurs intracellularly as well as extracellularly (Carlson et al., 2004), for example in exosomes in urine (Pisitkun et al., 2004). Exosomes are derivatives of so-called "multivesicular bodies" and may play an alternative, but decisive role in the antigen presentation of immune cells (Schartz et al., 2002). The exosomes detected in urine are possibly identical to the so-called prostasomes described already at an earlier date (Arienti et al., 2004; Utleg et al., 2003), in any case, both contain ANXA3.

Protein biomarkers for therapy or diagnostics of prostate cancer and other epithelial cancers of urogenital tract are described in US 2005 130 876, WO 03 086 461, WO 2005 078 124, EP 05 011 042.8 and EP 05 026 092.6.

Previous methods for the determination of ANXA3, however, suffer from the low specificity of available antibodies which show considerable crossreactivity towards other annexins. Thus, the object of the present invention was to provide a method for determining prostate carcinoma allowing a highly specific diagnosis in an early stage of the disease.

In a first aspect, the present invention refers to a method for the diagnosis of cancer wherein a sample is analyzed for the presence and/or amount of annexin A3 (ANX A3) with an antibody specific for annexin A3 which has a low crossreactivity against other annexins.

A further aspect of the present invention is a test reagent for the diagnosis of cancer comprising at least one antibody specific for annexin A3 which has a low crossreactivity against other annexins.

Still a further aspect of the invention is a pharmaceutical composition comprising as an active agent an antibody specific for annexin A3 which has a low crossreactivity against other annexins for the manufacture of a medicament for the treatment of cancer.

Still a further aspect of the invention is an antibody specific for annexin A3, which has a low crossreactivity against other annexins.

Still a further aspect of the present invention is a cell, particularly a hybridoma cell producing an antibody as described above.

The term "antibody" as used in the present application also encompasses antibody fragments having at least one antigen binding domain such as Fab fragments or F(ab')$_2$ fragments or recombinant antibodies such as single chain antibodies or fragments thereof such as Fv fragments.

Preferably, the antibody has no detectable crossreactivity against other annexins such as annexin 5, annexin 6 and/or annexin 8 as determined by densitometric analysis of Western Blots after silver staining. Preferably, the antibody is a monoclonal antibody or a mixture of monoclonal antibodies. The monoclonal antibody may also be a chimeric monoclonal antibody or humanized monoclonal antibody obtainable by humanizing non human constant and optionally variable framework regions. Some high-specific polyclonal antisera, however, are also suitable in the method of the present invention.

Preferred monoclonal antibodies may be obtained by immunizing an experimental animal, e.g. a mouse, rat, rabbit etc with purified ANXA3 or fragments thereof, particularly N-terminal fragments thereof and obtaining hybridoma cells producing desired monoclonal antibodies according to standard methods. More preferably, the antibody is directed against an epitope in the N-terminal region of human annexin A3 (also designated as Annexin III, Lipocortin III, Placental anticoagulant protein III (PAP-III), 35-alpha calcimedin, or Inositol-1,2-cyclic phosphate-2-phosphohydrolase), particularly in the region of amino acids 1-16 of human annexin A3 (GenBank Accession No. P12429). Preferably, the antibody binds to the surface of cancer cells.

Preferred monoclonal antibodies may be obtained by immunizing an experimental animal, e.g. a mouse, rat, rabbit, etc. with purified ANXA3 or fragments thereof, particularly fragments including the 16 N-terminal amino acids, e.g. fragments like ANX A3 (AA 1-324), ANX A3 (AA 1-159) or ANX A3 (AA 1-106); and obtaining hybridoma cells producing desired monoclonal antibodies according to standard methods. As explained above, monoclonal antibodies having a desired specificity may be obtained by screening procedures employing the above or similar fragments for epitope mapping and corresponding selection of monoclonal antibodies specifically binding to N-terminal parts of ANXA3. Especially preferred is also the use of native human ANXA3, e.g. isolated from human neutrophils as an immunogen for the generation of monoclonal antibodies.

Further, preferred monoclonal human antibodies directed against ANXA3 may be obtained from human individuals, e.g. human cancer patients or other individuals. Antibody-producing B-cells may be isolated from said individuals according to standard methods.

In an especially preferred embodiment, the antibody is a monoclonal antibody selected from an antibody produced by the hybridoma cell lines tgc 5 ProII6G7(DSM ACC2778), tgc 6 ProIII1G11(DSM ACC2779), tgc 7 ProVII5C5(DSM ACC2780), tgc 8 ProIII1E1(DSM ACC2781), tgc 13 ProI/5G9, tgc 12 ProIII/4B11, tgc 14 ProVIII/3D7 or an antibody which binds to the same epitopes on annexin A3. Antibodies binding to the same epitopes may be determined by competition experiments according to standard protocols. The above hybridoma cell lines have been deposited on 5 May 2006 (DSM ACC2778, DSM ACC2779, DSM ACC2780 and DSM ACC2781) and on 5 Jun. 2007 (tgc 13 ProI/5G9, tgc 12 ProIII/4B11, tgc 14 ProVIII/3D7) at DMSZ (Deutsche Sammlung für Mikroorganismen und Zellkulturen GmbH), Mascheroder Weg 1b, D-38124 Braunschweig, according to the Budapest Treaty.

In a further preferred embodiment, the antibody is a monoclonal antibody directed against an epitope on annexin A3 comprising a sequence selected from

| (i) | VRDYPDFSPSVD; | (SEQ ID NO: 1) |
|---|---|---|
| (ii) | MLISILTERSNA; | (SEQ ID NO: 2) |
| (iii) | GDFRKALLTLADGRRDESLKVDEHL AKQ; | (SEQ ID NO: 3) |
| (iv) | KLTFDEYRNISQKDIVDSIKGELSG; | (SEQ ID NO: 4) |
| (v) | IMVSRSEIDLLDIRTEF; | (SEQ ID NO: 5) |
| (vi) | YSAIKSDTSGDYEITLL | (SEQ ID NO: 6) | or a partial contiguous sequence thereof with a length of at least 6 amino acids.

An especially preferred partial sequence of SEQ ID NO:1 is DYPDFSPSV [SEQ ID NO: 7]. An especially preferred partial sequence of SEQ ID NO:2 is LISILTERS [SEQ ID NO: 8]. An especially preferred partial sequence of SEQ ID NO:3 is FRKALL [SEQ ID NO:9] or SLKVDEHLA [SEQ ID NO:10]. An especially preferred partial sequence of SEQ ID NO:4 is TFDEYRNIS [SEQ ID NO:11]. An especially preferred partial sequence of SEQ ID NO:5 is SRSEIDLLD [SEQ ID NO:12]. An especially preferred partial sequence of SEQ ID NO:6 is AIKSDTSGDYEI [SEQ ID NO:13]. An example of an antibody directed against an epitope in SEQ ID NO:1 is tgct ProVII 5C5 (DSM ACC2780. Examples of antibodies directed against an epitope in SEQ ID NO:2 are tgc5 ProII 6G7 (DSM ACC2778) and tgc6 ProIII 1611 (DSM ACC2779). Examples of antibodies directed against the epitopes in the C-terminal region of human ANXA3 are tgc 13 ProI/5G9, tgc 12 ProIII/4B11 and tgc 14 ProVIII/3D7. In particular, preferred antibodies are directed against an epitope in SEQ ID NO:5 and/or SEQ ID NO:6.

Further antibodies directed against epitopes in SEQ ID NO:1-6 may be obtained by immunizing an experimental animal with polypeptides or peptides comprising the epitope sequences, e.g. recombinant human ANXA3, homologous polypeptides from other species or fragments thereof.

The cancer which may be diagnosed according to the present invention is preferably a cancer of the urogenital and/or gastro-intestinal tract, such as cancer of prostate, bladder, kidney, urethra, ovaria, uterus or colon. Particularly, the cancer is an epithelial cancer. In an especially preferred embodiment the cancer is prostate cancer.

The method of the present invention may be carried out in any test format suitable for immunological determinations. In some test formats it may be preferred to use an antibody which carries a labelling group, e.g. a visual marker, such as a latex or gold bead, a fluorescence marker group, an enzymatic marker group etc. Conjugates of antibodies and labelling groups may be produced according to standard methods, e.g. by covalent coupling to reactive amino acid side groups of the antibody such as carboxy, amino and/or thiol groups with labelling groups, e.g. via bifunctional spacer molecules.

The sample is preferably obtained from a human subject. In a particularly preferred embodiment, the method of the invention is a non-invasive diagnostic procedure, wherein the sample may be e.g. a urine sample, particularly an exprimate urine sample or a faeces sample. If desired, the sample may be subjected to pretreatment procedures, e.g. gel filtration.

The sample may be subjected to a fractionation procedure which allows separate determination of extracellular and intracellular ANXA3. For example, the sample may be centrifuged in order to obtain a cell pellet and a supernatant whereby intracellular annexin A3 is determined in the cell pellet and extracellular annexin A3 is determined in the supernatant. In an especially preferred embodiment the method comprises a selective determination of extracellular ANXA3.

In a further embodiment, the method of the invention may be a histochemical procedure wherein the sample may be a tissue sample, particularly a biopsy, e.g. a punch biopsy. In a histochemical procedure, a selective determination of extracellular ANXA3 may be carried out by determining the localisation of ANXA3 within the sample.

In the method of the invention, a sample is classified as indicative for cancer, e.g. prostate cancer when the abundance of extracellular ANXA3 is decreased in supernatants of the sample, e.g. the exprimate urine after low speed centrifugation or in corresponding pellets, when compared to non-cancer patients with a variety of conditions ranging from benign prostatic hyperplasia (BPH), fibrosis, chronic prostatitis, prostatic intraepithelial neoplasia of various stages (PIN1-3). In comparison to completely healthy patients, abundances of ANXA3 appear to be increased in both pellets and supernatants. Taken together, any type of ratio or combination of ANXA3 total amounts or concentrations in supernatants and/or pellets of exprimate urine, which is used for diagnostic discrimination of the various conditions mentioned, is comprised by the present invention.

The present invention covers essentially any set of cut-offs concerning ANXA3 abundances in various intracellular and extracellular sample fractions, e.g. of exprimate urine, accessible by any type of differential centrifugation and related ratios for diagnostic purposes.

The method of the present invention may additionally comprise the determination of further cancer markers, e.g. cancer markers. The determination of further markers may be carried out in the same sample where ANXA3 is determined or in different samples, e.g. blood, serum and/or plasma samples. Especially preferred is the determination of blood, serum or plasma markers, in particular of at least one member of the kallikrein protease family, such as prostate specific antigen (PSA) and/or at least one epithelial cell marker, particularly prostate specific membrane antigen (PSMA).

The diagnostic method of the invention may include a determination of the disease stage, wherein differentiation between a precancerous stage such as PIN and a cancerous disease stage is carried out. A determination of a disease stage is based on histological classification by clinical pathologists, the standard classification of prostate cancers is according to Gleason scores, but there are other staging methods grouping cancers into three groups of increasing severity. So far these staging methods rely heavily on morphological criteria and require experienced experts. For non-cancer cases the above mentioned conditions ranging from benign prostatic hyperplasia (BPH), fibrosis, chronic prostatitis, prostatic intraepithelial neoplasia of various stages (PIN1-3) have been described. The present invention relates to any type of stratification of prostate cancer or prostate-related non-cancerous stages by using an ANXA3-related read-out with appropriate set of cut-offs from any type of fraction of exprimate urine or any other sample.

The present invention also refers to the use of the above antibodies in pharmaceutical applications, e.g. for the manufacture of a medicament for the treatment of cancer, particularly cancer of the urogenital and/or gastro-intestinal tract as described above, more particularly prostate cancer. In this embodiment of the invention, the antibody is preferably a chimeric or humanized monoclonal antibody having constant human regions, e.g. constant human IgG1, IgG2, IgG3 or IgG4 regions and optionally humanized framework regions.

Alternatively, the antibody may be a human antibody which may be obtained from the serum of human individuals. The therapeutic antibody preferably binds to the surface of cancer cells, e.g. prostate cancer cells.

The therapeutic antibody may be conjugated to an effector molecule, e.g. a radioactive and/or cytotoxic moiety. For therapeutic applications the antibodies may be administered in a therapeutically effective dose of e.g. 10 to 5000 µg per day up to 4000 to 1000 µg per day preferably administered by infusion, depending on the type and severity of disease. The antibodies may be administered by known methods, e.g. parenterally according to standard protocols known for the administration of other antibodies such as Trastuzumab, Rituximab, Cetuximab etc. The administration of the antibodies may be combined with other therapeutic options, e.g. administration of other anti-tumor antibodies, administration of cytotoxic agents, surgery and/or radiation therapy.

Further, the present invention shall be explained in more detail by the following Figures and Examples.

EXAMPLES

Example 1

Production of Specific Monoclonal Antibodies Directed Against ANXA3

Figure 1:
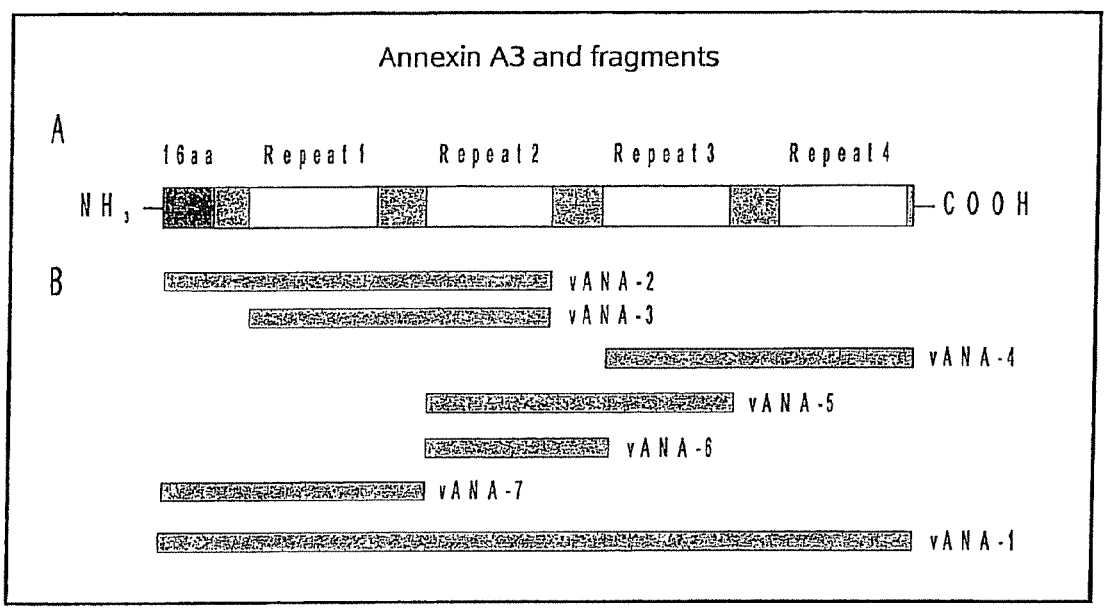
FIG. 1: Overview of structure of annexin A3 (A) and recombinant fragments of annexin A3 used for epitope mapping of monoclonal antibodies; based on this type of screening by epitope mapping the monoclonal antibodies which are subject of the present patent application have been selected (B).

Recombinant soluble fragments of human annexin A3, vANA-5 (AA 107-243), vANA-7 (AA 1-106), vANA-1 (AA 1-324), vANA-2 (AA 1-159), vANA-3 (AA 35-159), vANA-4 (AA 191-324) and vANA-6 (AA 107-190) were cloned and expressed in *E. coli* and subsequently chromatographically purified. An overview of the structure of annexin A3 and recombinant fragments thereof is shown in FIG. 1.

Figure 2:
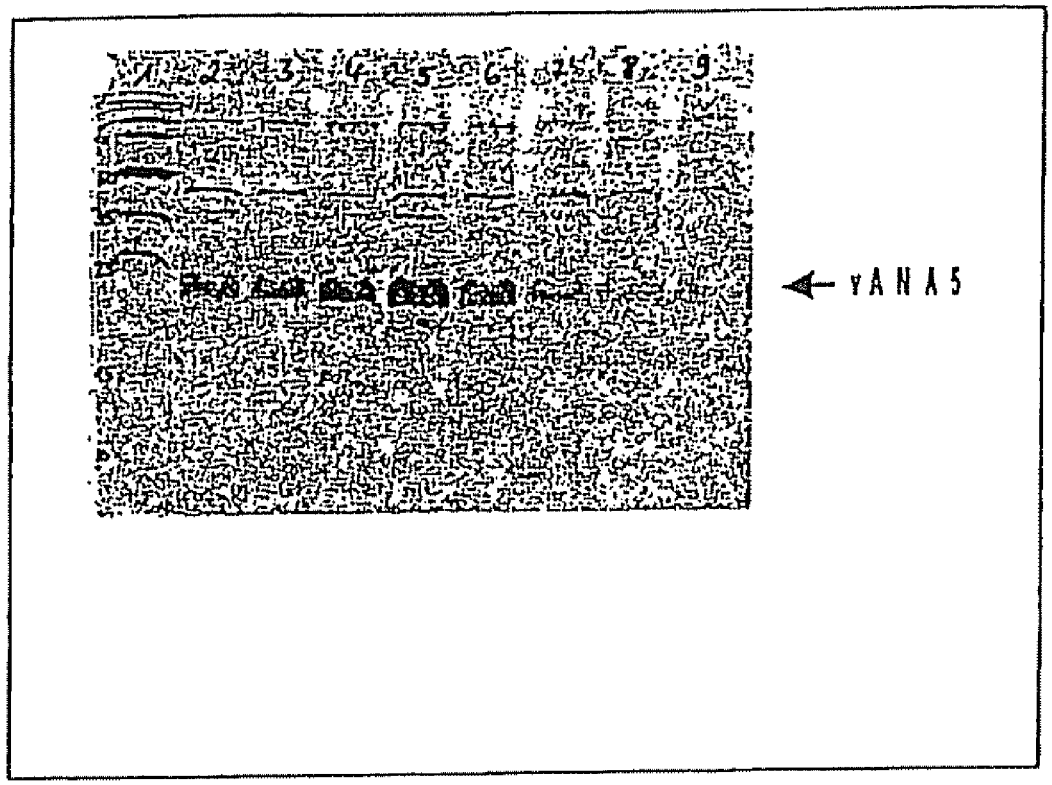
FIG. 2: Purification of human annexin A3 fragment vANA-5 (amino acids 107-243): SDS-PAGE chromatographically purified vANA-5.
Figure 3:
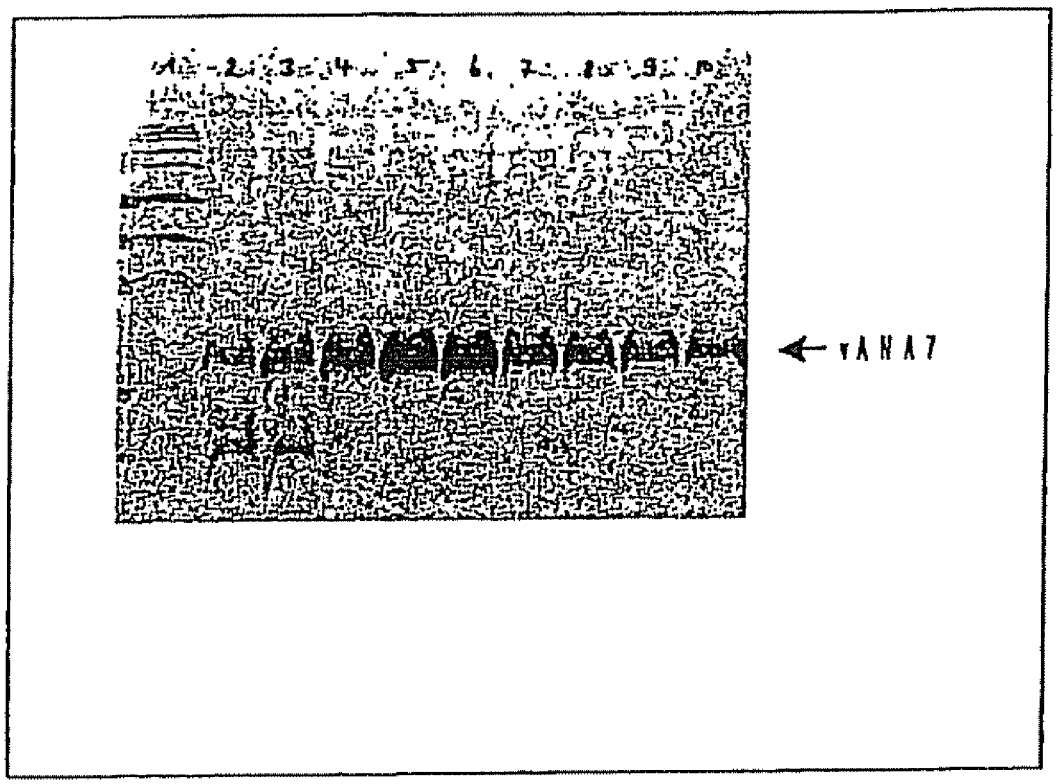
FIG. 3: Purification of human annexin A3 fragment vANA-7 (amino acids 1-106): SDS-PAGE chromatographically purified vANA-7.
Figure 4:
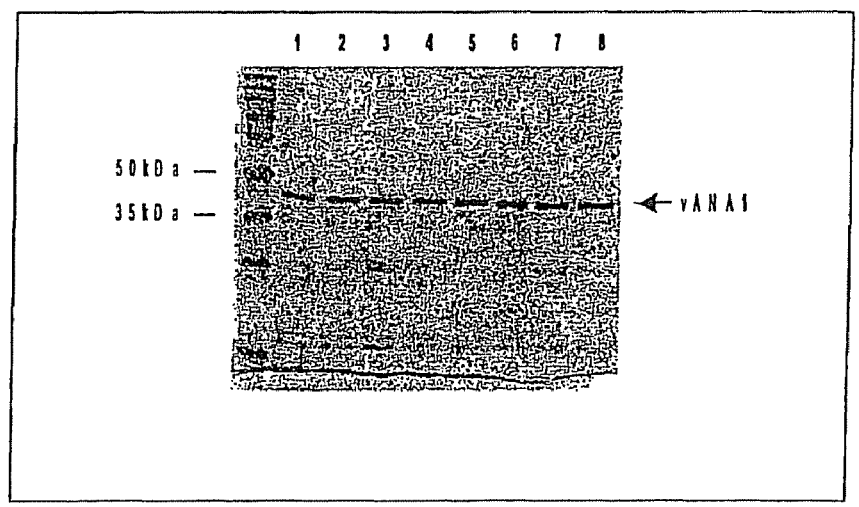
FIG. 4: Purification of annexin A3 fragment vANA-1 (amino acids 1-324): SDS-PAGE of chromatographically purified vANA-1.

FIGS. 2, 3 and 4 show Coomassie-stained 1D gels of recombinant soluble ANXA3 fragments vANA-5, vANA-7 and vANA-1 purified by standard chromatographic procedures.

Figure 5:
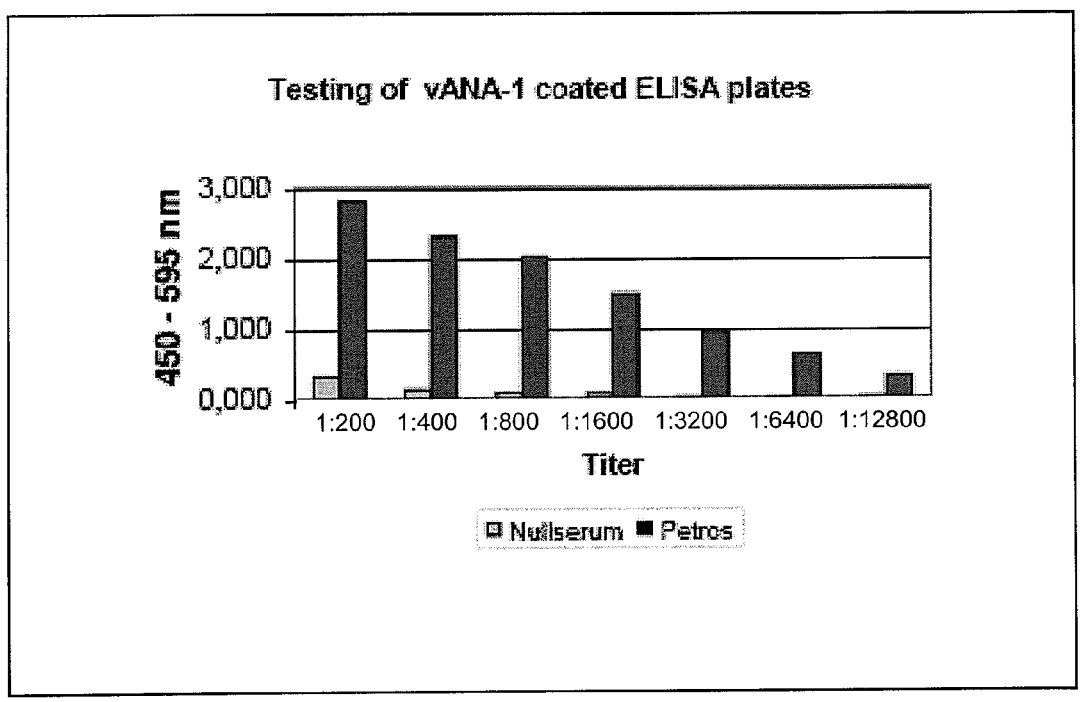
FIG. 5: Testing of the vANA-1 ELISA plate: 'Petros': Annexin A3-specific. antiserum; 'Nullserum': premium serum from rabbit.

The screening for positive hybridoma cells after fusion and during cloning of antibody-producing cells, an anti-annexin A3 ELISA based on fragment vANA-1 was developed (FIG. 5). To achieve inclusive recognition of antibodies which bind to native epitopes of ANXA3, recombinant vANA-1 was renatured before coupling to ELISA plates. Recombinant vANA-1 was coated at a concentration of 1 µg/well to ELISA plates. The functionality of ELISA plates was checked with polyclonal anti ANXA3 serum.

Figure 6:
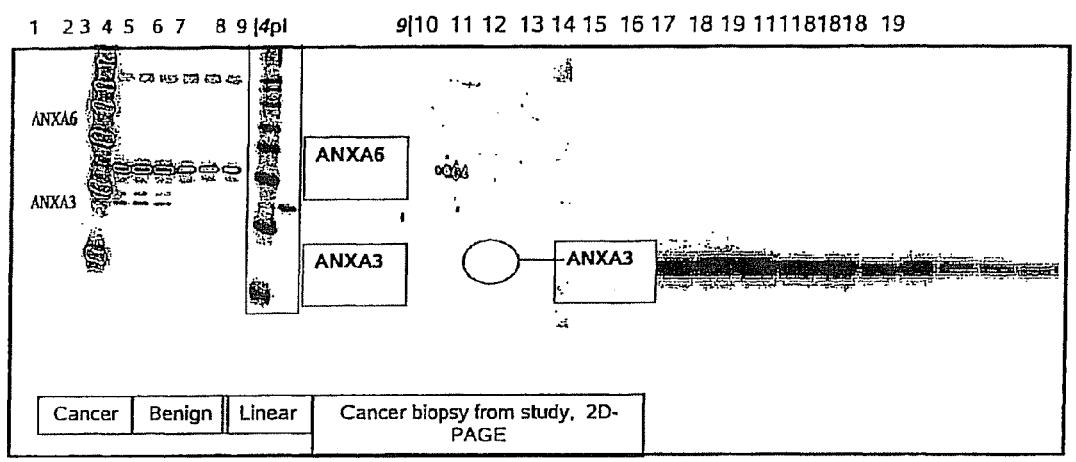
FIG. 6: Specificity of anti-ANXA3 antibodies: lanes 1-9 and the 2D-Western blot are taken from Wozny et al., 2006; lanes 10-19 show the various monoclonal anti-ANXA3 antibodies as explained in the text. They show virtually no cross-reactivity to any other protein of other annexins.

FIG. 6 shows false spectral colour depiction of the reactivity of polyclonal serum to a benign and a cancerous sample of prostate tissue. The cancerous sample is shown blotted by 2D-PAGE. The vast majority of the signal is obtained from a chain of four spots, which were identified by mass spectrometry as ANXA3. These false spectral colour images reflect a far deeper dynamic range than is permitted by single colour greyscales. The intensity of non-ANXA3 signals is always close to background, being represented by blue (close to background) pixels. The extent of this contrast between specific and non-specific signals is shown in the lanes 8 and 9 of FIG. 6, which present the results in single colour greyscale. This situation is further highlighted by the signal profiles of lanes 10 to 19 of various dilutions of monoclonal antibodies tgc5 Pro II6G7=DSM ACC2778 (lanes 10&11); tgc6 ProIII1G11 (DSM ACC2779) (lanes 15 & 16); tgc7 ProVII5C5 (DSM ACC2780) (lanes 12-14); tgc8 ProIII1E1 (DSM ACC2781) (lanes 17-19); which show an even lower cross reactivity.

As shown in FIG. 6, the monoclonal antibodies which are subject of the present invention, have essentially no cross-reactivity with other annexins. Whereas the polyclonal serum from Wozny et al. 2006 has some residual cross-reactivity with ANXA6, the staining with monoclonal antibodies (of a biopsy from a prostate cancer patient and of a prostate cancer cell line, PC3) shown on the right side of FIG. 6, produces less than 1% background staining at other positions than 33 kD for ANXA3.

Figure 7:
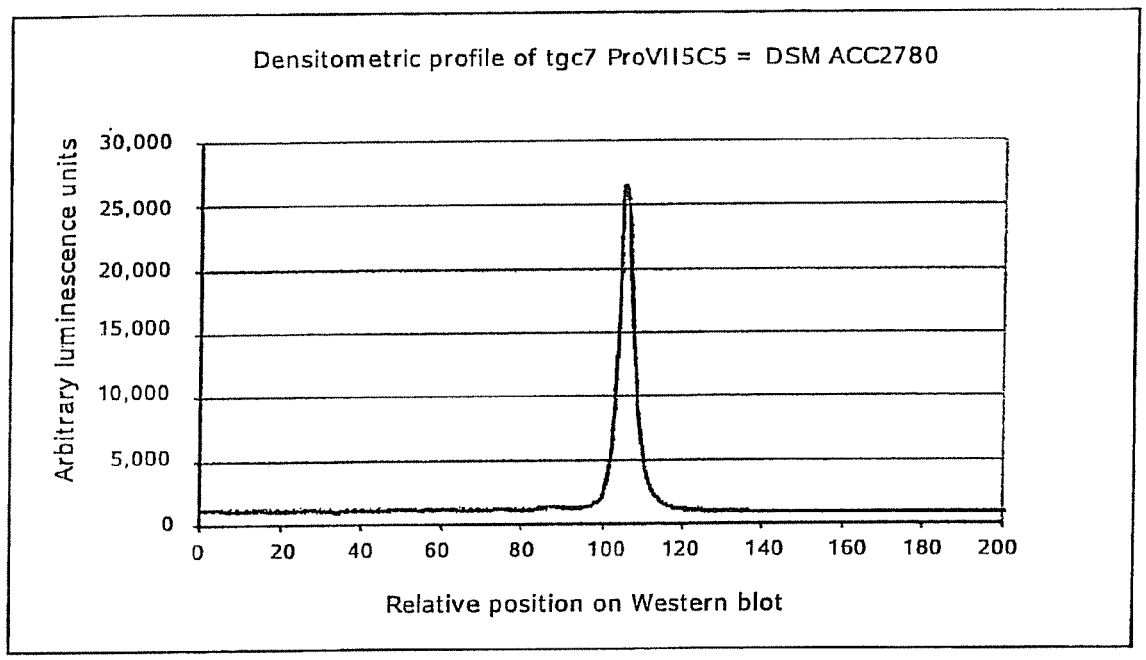
FIG. 7: The densitometric quantification of anti-ANXA3-staining after ECL development of Western blots of total cell lysates from PC3 cells shows the high specificity of monoclonal antibody tgc7 ProVII5C5 (DSM ACC2780).

FIG. 7 shows a densitometric quantification of anti-ANXA3 staining after electrochemiluminescence (ECL) development. A Western blot of total cell lysates from PC3 cells was analyzed with the antibody tgc7 ProVII5C5 (DSM 2780). Only a single band corresponding to ANXA3 was found. There is virtually no crossreactivity.

Example 2

Determination of Antibody Specificity in Exprimate Urine Samples and Tissue Sections The monoclonal antibodies of Example 1 were used in an ELISA format as described above to detect ANXA3 in supernatants from exprimate urine from cancer patients.

Figure 8:
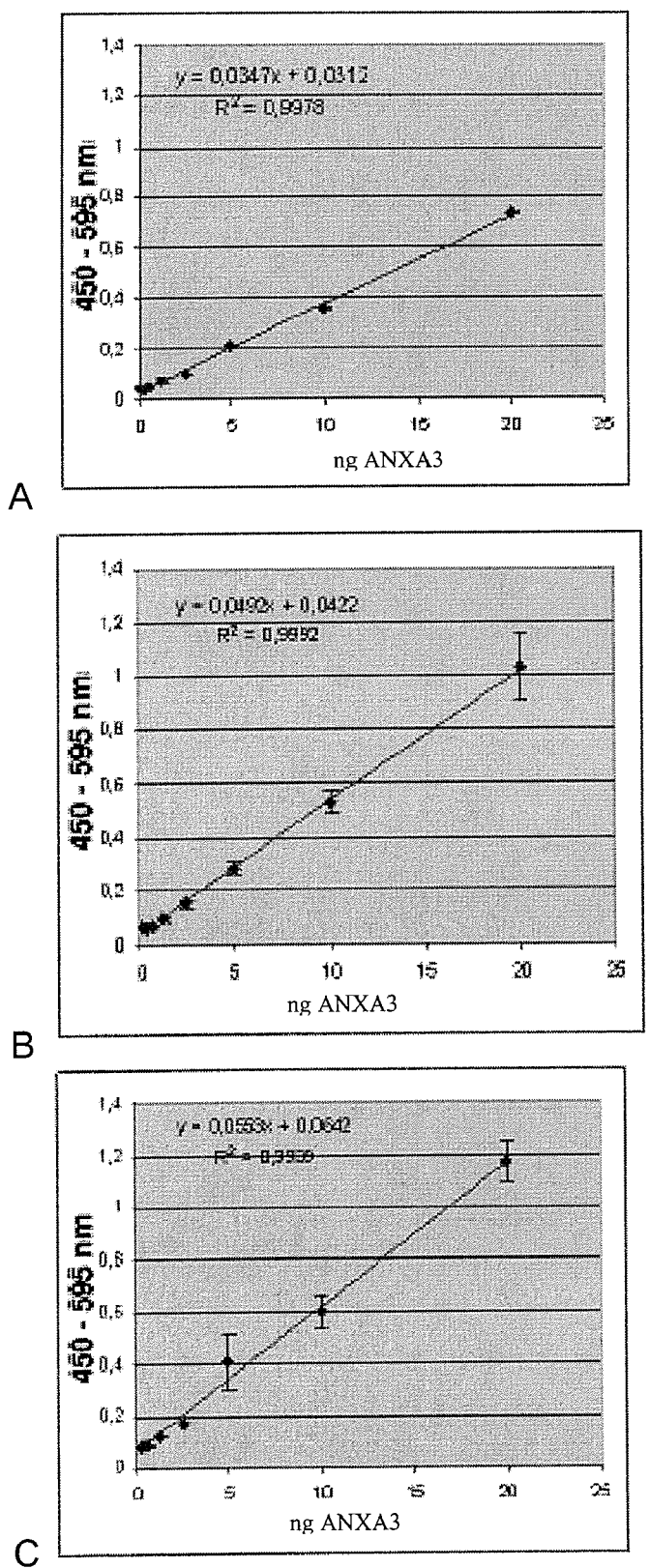
FIG. 8: Calibration of anti-ANXA3-based ELISA with vANA-1 as antigen, the colour reaction was stopped after 15 (A), 30 (B) and 45 (C) min.

As shown in FIG. 8, for calibration, ELISA-plates were coated with tgc7 ProVII5C5 (DSM ACC2780), and a dilution series of vANA-1 (20-0.3 ng/well) was detected, using biotinylated tgc5 Pro II6G7 (DSM ACC2778) and avidin-HRP with TMB as substrate. The enzymatic colour reaction was stopped after 15, 30 and 45 min as indicated.

Figure 9:
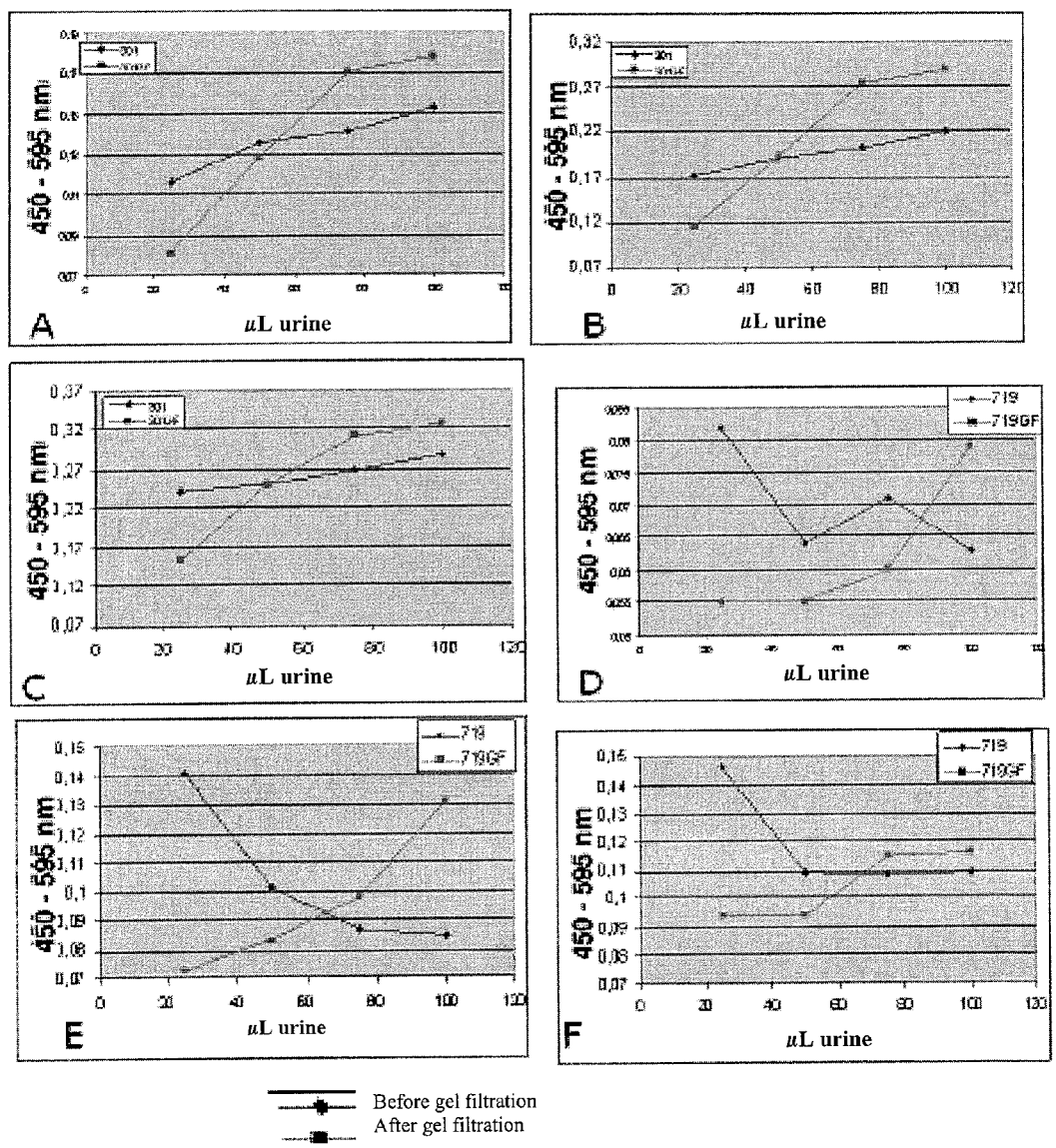
FIG. 9: Detection of ANXA3 in exprimate urine supernatants after standard low speed centrifugation; A, D: 15 min; B, E: 30 min. and C, F: 45 min. of development.

In FIG. 9, the detection of ANXA3 in supernatants of exprimate urine taken from patients is shown. The sample was centrifuged according to standard clinical procedures with a low speed centrifugation. The signals were improved by prior gel filtration (GF), which essentially removes urea, which might interfere with Western blots from 1D PAGE.

The antibodies were also tested in an immunohistochemical staining procedure of tissue sections. A high intracellular concentration of ANXA3 was found in normal prostate epithet. During disease progress from PIN to carcinoma, an apparent local increase of extracellularly localized ANXA3 is found. These stained regions of biopsies, however, do not represent or allow general estimates of quantitative relationships of diagnostic ANXA3 distributions between supernatants and pellets of exprimate urine. This is simply because biopsies are rather qualitative, but cannot comprehensively represent prostate areas of cancerous of benign quality.

Example 3

Clinical Study for the Determination of ANXA3 in Exprimate Urine Samples

A multicentre blinded clinical study was carried out in order to determine the sensitivity and specificity of a prostate carcinoma diagnosis based on a non-invasive detection of ANXA3 in body fluids, particularly in exprimate urine.

3.1 Patients and Controls

A: Patients with histologically verified prostate carcinoma (PCA group): n=about 200.

B: Patients without prostate carcinoma as determined by histologic testing (control group): n=about 300.

3.2 Taking and Processing of Samples 3.2.1 Serum/Plasma

A serum tube for the routine determination of the serum PSA value was taken intravenously. Further, 1-2 ml serum were additionally asserved and stored deep-frozen. This blood sample was further analysed for PSA. The taking of the blood sample took place before prostate punch biopsies or a rectal palpation were carried out.

3.2.2 Exprimate Urine Sediment

Following 20 s palpation and massaging of the prostate, the patient was requested to empty his bladder. The obtained exprimate urine was processed according to published procedures (I. Rehman, A. R. Azzouzi, J. W. F. Catto, S. Allen, S. S. Cross, K. Feeley, M. Meuth, & F. C. Hamdy, Proteomic analysis of voided urine after prostatic massage from patients with prostate cancer: A pilot study, Urology 64 (6), 2004, 1238-1243; C. Goessl, M. Müller, R. Heicappell, H. Krause, B. Straub, M. Schrader & K. Miller, DNA-based detection of prostate cancer in urine after prostatic massage. Urology 58 (3), 2001, 335-338) and the products were stored at −80° C.

Like the serum, the exprimate urine has got to be taken, if possible, before prostate punch biopsies are carried out.

3.3 Results

In about 200 PSA positive patients, the determination of ANXA3 in the sediments and supernatants of exprimate urine samples gave a sensitivity of about 90% and a specificity of about 80%.

Figure 10:
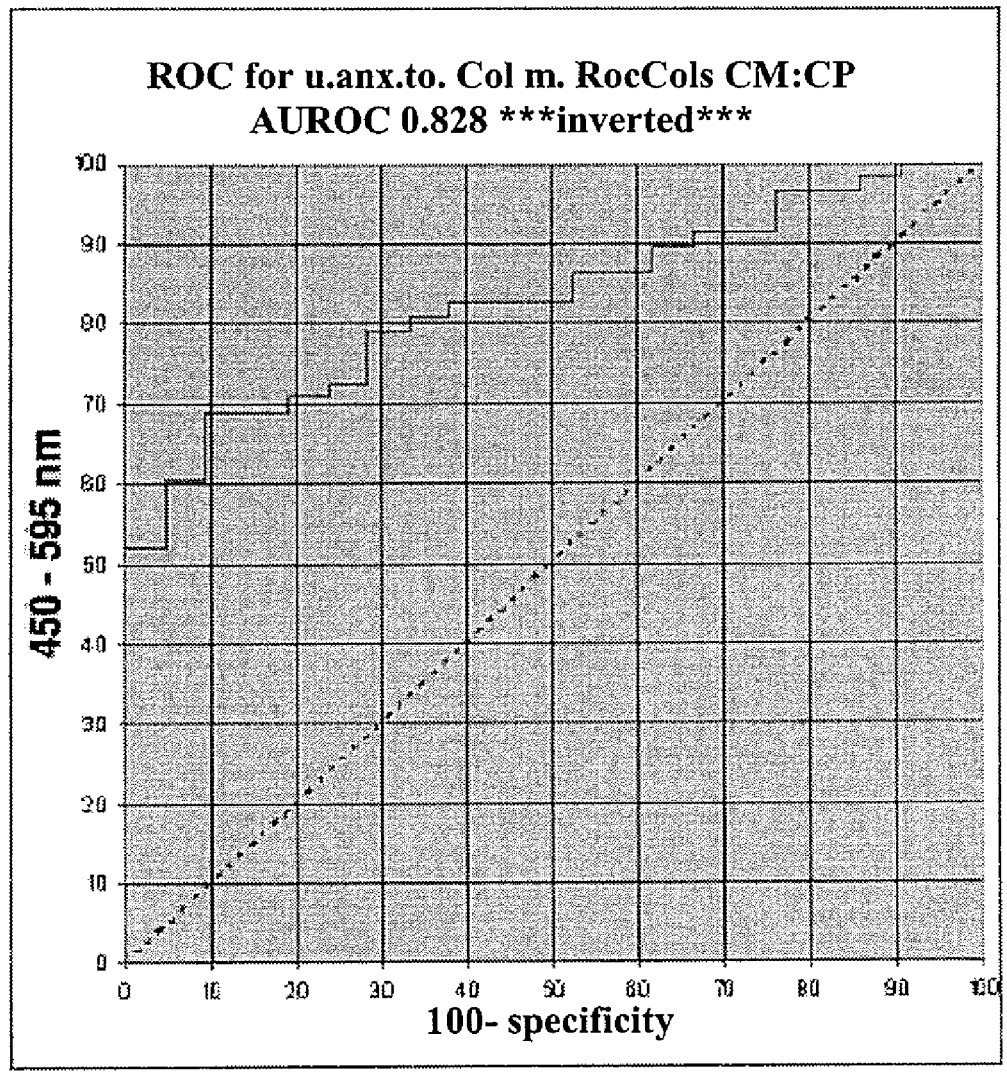
FIG. 10: ROC curve for anti-ANXA3-based diagnostic study, employing an ELISA as shown in FIG. 6 and based on 200 patients with PSA-values in the range of 4-10 ng/ml; AUROC is 0.823, indicating 90% specificity at 70% sensitivity for this important collective in the PSA "grey zone".

As shown in FIG. 10, the ROC-values for read-outs based on ANXA3 in supernatants (u.anx.tot) in patients with PSA in the range of 2-6 ng/ml were 0.8, in the range of PSA-values of 4-10 ng/ml, ROC values were 0.85 and in total collective of all patients and all ranges of PSA-values, ROC-values for ANXA3 were 0.74.

The representative ROC curve in FIG. 10, for those patients with a PSA value between 4 and 10 ng/ml; shows a diagnostic relevance in particular in this important grey zone of PSA (where the specificity of PSA is exceedingly low (Roddam A W, Duffy M J, Hamdy F C, Ward A M, Patnick J, Price C P Rimmer J, Sturgeon C, White P, Allen N E; On behalf of the NHS Prostate Cancer Risk Management Programme. Use of prostate-specific antigen (PSA) isoforms for the detection of prostate cancer in men with a PSA level of 2-10 ng/ml: systematic review and meta-analysis. Eur Urol. 2005 September; 48 (3):386-99; discussion 398-9. Review. PMID: 15982797; Stamey T A, Caldwell M, McNeal J E, Nolley R, Hemenez M, Downs J. The prostate specific antigen era in the United States is over for prostate cancer: what happened in the last 20 years? J Urol. 2004 October; 172(4 Pt 1):1297-301. PMID: 15371827)), ROC curves are a standard tool of clinical statistics and well described, e.g. at www.anaesthetist.com/mnm/stats/roc/.

Example 4

Binding of Monoclonal Antibodies to Cancer Cells

The monoclonal anti-ANXA3 antibodies are suitable as surface markers in diagnostic (pathological histologies) and therapeutic applications.

As shown in the following by flow cytometry, in particular the monoclonal antibody specifically binding to the N-terminal epitope, tgc7 ProVII5C5 (DSM ACC2780), binds to extracellular binding sites of a prostate cancer cell line (PC-3 cells, ATCC, DCV-1017, Version 08-2004) in a calcium-dependent manner.

Unspecific binding was assessed during each experiment by incubation with secondary antibody alone and by employing unspecific and unrelated control antibodies (monoclonals and polyclonals).

Figure 11:
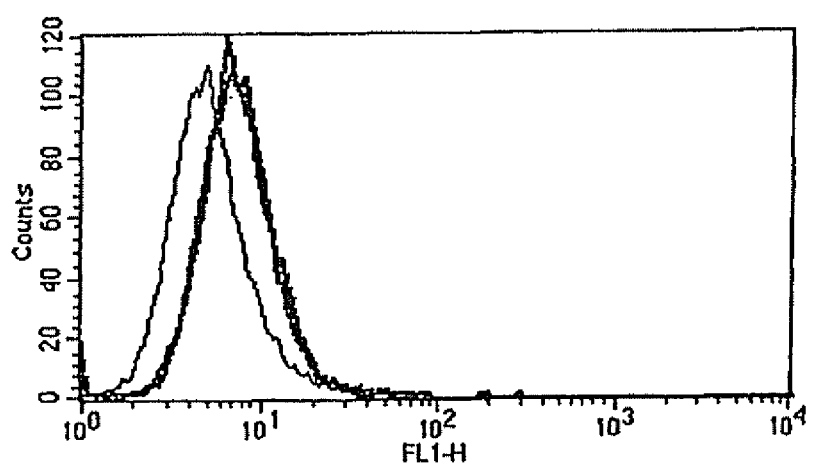
FIG. 11: The polyclonal serum used in Wozny et al., 2006 (see FIG. 1), only insignificantly binds to surfaces of PC-3 cells.

FIG. 11 shows that the polyclonal serum used in Wozny et al., 2006 (see FIG. 6), only insignificantly binds to surfaces of PC-3 cells.

Cells were rinsed with an appropriate buffer and incubated on ice for 30 min at dilutions indicated in FIG. 11. Subsequently, all samples were incubated with 100 µl of a 1:50 dilution of FITC-coupled anti-rabbit secondary antibody. After washing steps 12,000 cells of each sample were analysed by flow cytometry as shown.

In essence the polyclonal serum did not result in a significant increase of fluorescence intensity at a variety of dilutions and in comparison to control sera. Surface expression of ANXA3 on PC-3 cells can thus not be shown at this stage, probably because the concentration of specific antibodies in the polyclonal serum is too low.

Figure 12:
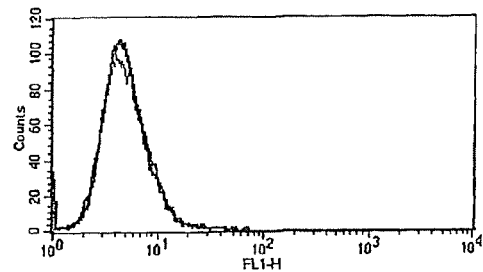
FIG. 12: Detection of surface-ANXA3 on PC-3 cells by tgc7 ProVII5C5 (DSM ACC2780); the antibody was used at concentrations indicated in the graphs. As secondary antibody, anti-mouse-IgG-FITC in a dilution of 1:50 was employed, the staining volume was 100 µl of antibody dilution. These results indicate a surface localisation of ANXA3 in this prostate cancer cell line, which can potentially be exploited therapeutically.
Figure 12:
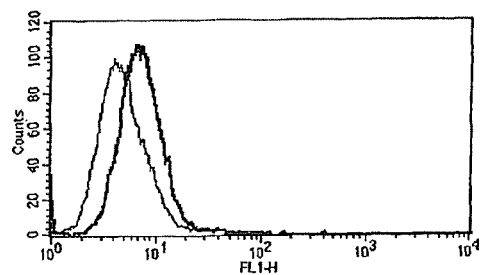
Figure 12:
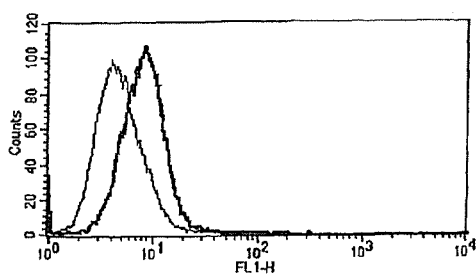

However, as shown in FIG. 12, the monoclonal antibody tgc7 ProVII5C5 (DSM ACC2780), binds indeed in a concentration- and calcium-dependent manner to surface epitopes of PC-3 cells.

Example 5

Epitope Mapping

Figure 13:
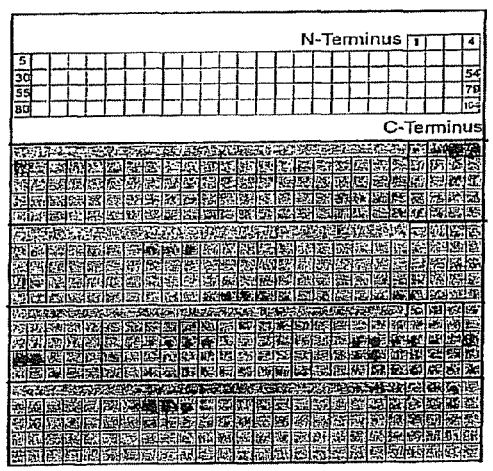
FIG. 13: Using overlapping peptide sequences covering the antigenic region of ANXA3, six epitopes were found and characterized as contributing to the highly specific binding of a polyclonal antiserum. Next to two epitopes in the N-terminal region (which are recognized by tgc5 Pro II6G7=DSM ACC2778; tgc6 ProIII1G11=DSM ACC2779; tgc7 ProVII5C5=DSM ACC2780), there are four more epitopes which are shown in more detail in FIG. 14.
Figure 14:
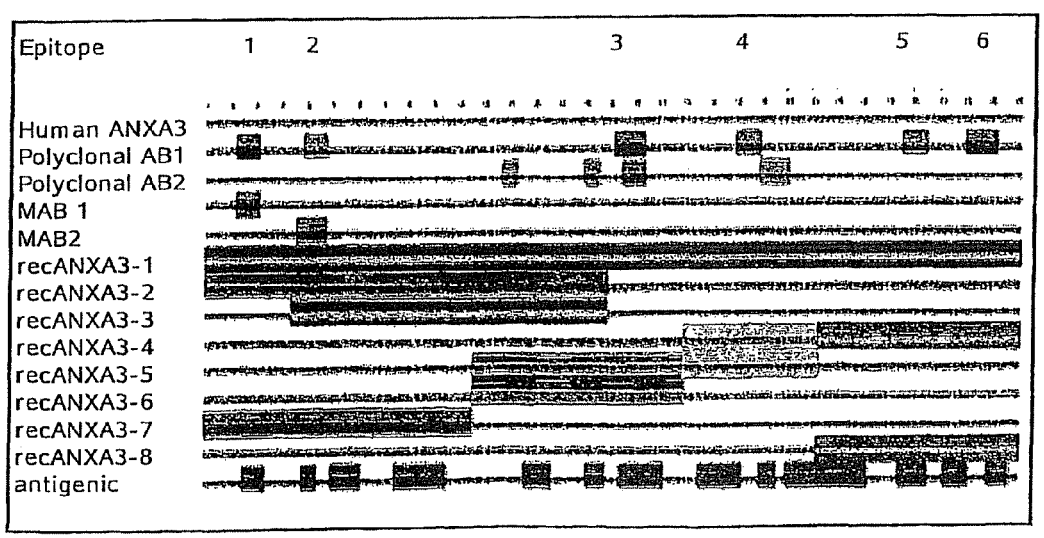
FIG. 14: Overview about the sequence of human ANXA3 and antigenic regions thereof (lowest line): Polyclonal AB1 is a highly specific polyclonal antiserum, exclusively binding to ANXA3, with no cross-reactivity to other annexins or any other antigens (as shown by 2D-Western blots and mass spectrometry, FIG. 1). Polyclonal AB2 is directed against epitopes 3 and 4; MAB1 is tgc7 ProVII5C5=DSM ACC2780 and MAB 2 stands for both tgc5 Pro II6G7=DSM ACC2778 and tgc6 ProIII1G11=DSM ACC2779; The recombinant ANXA3 fragments 1-8 were used for respective immunizations.
Figure 15:
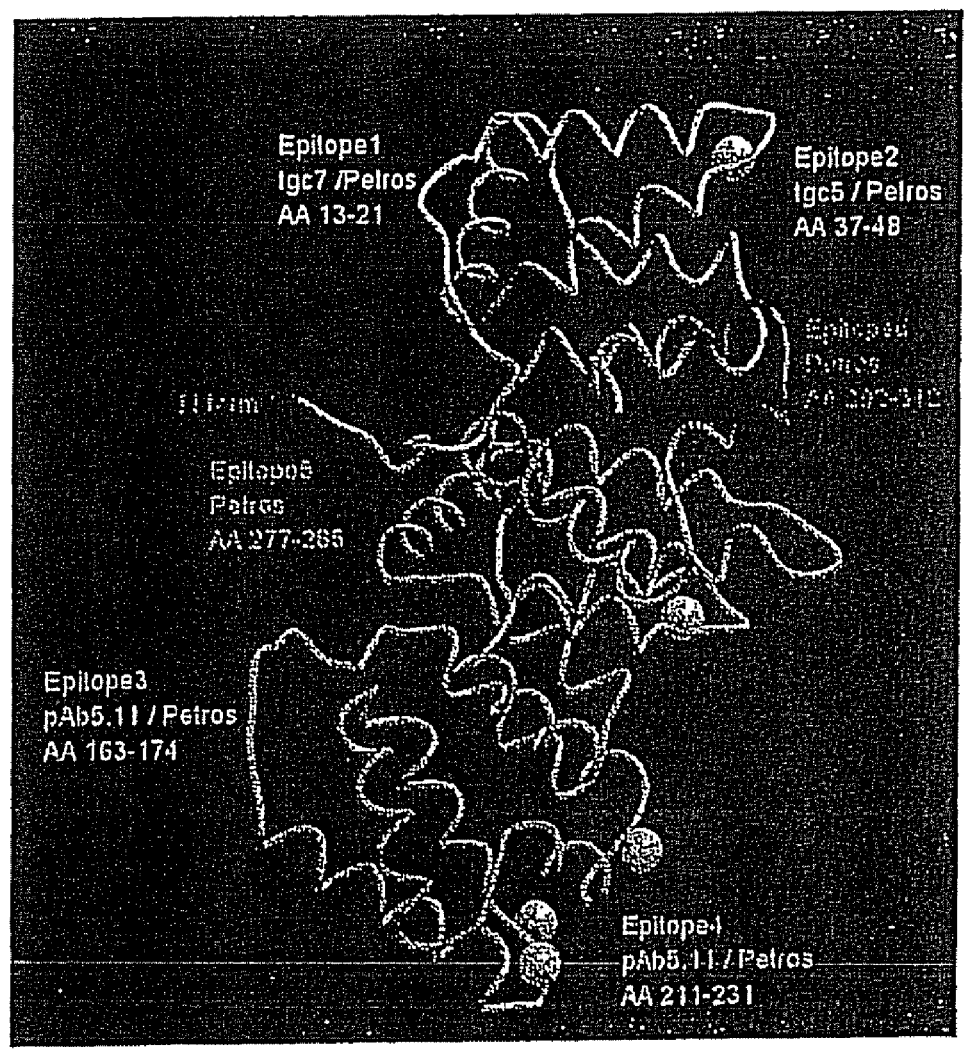
FIG. 15: Schematic depiction of the crystal structure of human ANXA3.

After using overlapping peptide sequences covering the whole antigenic region of Annexin A3 (ANXA3), we concluded that only six epitopes are responsible for high specificity binding as shown in FIGS. 13 and 14 by analyzing the binding of a highly specific polyclonal antibody (see FIG. 1). The specificity of the polyclonal antiserum was controlled by 2D-PAGE-derived Western blots and mass spectrometry. The same applied to monoclonal antibodies tgc5 Pro II6G7=DSM ACC2778; tgc6 ProIII1G11=DSM ACC2779; tgc7 ProVII5C5=DSM ACC2780; tgc 13 ProI/5G9; tgc 12 ProIII/4B11; tgc 14 ProVIII/3D7.

The epitope mapping showed that next to two epitopes in the N-terminal region, there are also contributions from 2 epitopes in the middle region and from 2 epitopes in the C-terminal region of ANXA3 (FIG. 13).

The localisation of these epitopes (designated as epitopes 1-6) on human ANXA3 is shown in FIG. 14.

The crystal structure of human ANXA3 shown as an overview in FIG. 14 www.pdb.org/pdb/files/1axn.pdb and www.pdb.org/pdb/explore.do?structureId=1AXN) implies that epitopes 1, 2, 5 and 6, together from a domain in a native fold of ANXA3. We therefore proceeded to isolate human ANXA3 from neutrophils and immunized rabbits with this material to obtain corresponding antibodies. These antibodies are directed against native ANXA3, we again screened and selected for highest specificity and those binding to domains comprising the corresponding epitopes 1, 2, 5 and 6 are particularly suitable for diagnostic and therapeutic purposes.

REFERENCES

1. Alavi A S, Soloway M S, Vaidya A, Lynne C M, Gheiler E L. Local anesthesia for ultrasound guided prostate biopsy: a prospective randomized trial comparing 2 methods. J Urol 2001; 166: 1343-1345.

2. Arienti G, Carlini E, Saccardi C, Palmerini C A. Role of human prostasomes in the activation of spermatozoa. J Cell Mol Med. 2004 January-March; 8(1):77-84.
3. Carlsson et al. Dominant prostasome immunogens for sperm-agglutinating autoantibodies of infertile men. J Androl. 2004; 25:699-705.
4. Djavan B, Zlotta A, Kratzik C, Remzi M, Seitz C, Schulman C C, Marberger M. PSA, PSA density, PSA density of transition zone, free/total PSA ratio, and PSA velocity for early detection of prostate cancer in men with serum PSA 2.5 to 4.0 ng/mL. Urology 1999; 54: 517-522.
5. Djavan B, Waldert M, Zlotta A, Dobronski P. Seitz C, Remzi M, Borkowski A, Schulman C, Marberger M. Safety and morbidity of first and repeat transrectal ultrasound guided prostate needle biopsies: results of a prospective european prostate cancer detection study. J Urol 2001; 166: 856-860.
6. Gerke V, Creutz C E, Moss S E. Annexins: linking Ca2+ signalling to membrane dynamics. Nat Rev Mol Cell Biol. 2005 June; 6(6):449-61.
7. Gerke V, Moss S E. Annexins: from structure to function. Physiol Rev. 2002 April; 82(2):331-71.
8. Greenlee R T, Murray T, Bolden S, Wingo P A. Cancer statistics. CA Cancer J 2000; 50: 7-33.
9. Haese A, Huland E, Graefen M, Hammerer P, Noldus J, Huland H. Ultrasensitive detection of prostate specific antigen in the followup of 422 patients after radical prostatectomy. J Urol 1999; 161: 1206-1211.
10. Huland H. Radical prostatectomy: options and issues. Eur Urol 2001a; 39 Suppl 1: 3-9.
11. Huland H. Editorial. J Urol 2001b.
12. Knox J J, Moore M J. Treatment of hormone refractory prostate cancer. Semin Urol Oncol 2001; 19: 202-211.
13. Irani J, Fournier F, Bon D, Gremmo E, Dore B, Aubert J. Patient tolerance of transrectal ultrasound-guided biopsy of the prostate. Br J Urol 1997; 79: 608-610.
14. Issa J P: CpG-island methylation in aging and cancer. Curr Top Microbiol Immunol 2000; 249: 101-118.
15. Issa M M, Bux S, Chun T, Petros J A, Labadia A J, Anastasia K, Miller L E, Marshall F F. A randomized prospective trial of intrarectal lidocaine for pain control during transrectal prostate biopsy: The Emory University experience. J Urol 2000; 164: 397-399.
16. Jung K, Stephan C, Elgeti U, Lein M, Brux B, Kristiansen G, Rudolph B, Hauptmann S, Schnorr D, Loening S A, Sinha P. Molecular forms of prostate-specific antigen in serum with concentrations of total prostate-specific antigen <4 microg/L: are they useful tools for early detection and screening of prostate cancer? Int J Cancer 2001; 93: 759-765.
17. Keller, E. T. et al., Prostate Karzinoma skeletal metastases: cross-talk between tumor and bone. Cancer Metastasis Rev. 20, 333-349. (2001).
18. Lujan G M, Paez B A, Gonzalez F I, Romero C I, Gomez de Vicente J M, Berenguer S A. Adverse effects of transrectal prostatic biopsy. Analysis of 303 procedures. Actas Urol Esp 2001; 25: 46-49.
19. Makinen T, Tammela T L, Hakama M, Stenman U H, Rannikko S, Aro J, Juusela H, Maattanen L, Auvinen A. Prostate cancer screening within a prostate specific antigen range of 3 to 3.9 ng./ml.: a comparison of digital rectal examination and free prostate specific antigen as supplemental screening tests. J Urol 2001; 166: 1339-1342.
20. Miller K, Weiβbach L (Hrsg.): Leitlinien zur Diagnostik von Prostatakarzinomen. Urologe A 1999 a; 38: 388-401.
21. Miller K, Weiβbach L (Hrsg.): Leitlinien zur Diagnostik von Prostatakarzinomen. Urologe A 1999 b; 38: 630-639.
22. Okihara K, Fritsche H A, Ayala A, Johnston D A, Allard W J, Babaian R J. Can complexed prostate specific antigen and prostatic volume enhance prostate cancer detection in men with total prostate specific antigen between 2.5 and 4.0 ng./ml. J Urol 2001; 165: 1930-1936.
23. Pitsitkun T, Shen R-F, Knepper M A. Identification and proteomic profiling of exosomes in human urine. PNAS 2004; 101: 13386-13373.
24. Rescher U, Gerke V. Annexins—unique membrane binding proteins with diverse functions. J Cell Sci. 2004 Jun. 1; 117(Pt 13):2631-9.
25. Schartz, N. E., Chaput, N., Andre, F. & Zitvogel, L. From the antigen-presenting cell to the antigen-presenting vesicle: the exosomes. Curr. Opin. Mol. Ther. 4, 372-381 (2002).
26. Stamey T A, Yang N, Hay A R, McNeal J E, Freiha F S, Redwine E. Prostate-specific antigen as a serum marker for adenoKarzinoma of the prostate. N Engl J Med 1987; 317: 909-916.
27. Wang, W., Xu, J. & Kirsch, T. Annexin-mediated Ca2+ influx regulates growth plate chondrocyte maturation and apoptosis. J. Biol. Chem. 278, 3762-3769. (2003)
28. Utleg A G, Yi E C, Xie T, Shannon P, White J T, Goodlett D R, Hood L, Lin B. Proteomic analysis of human prostasomes. Prostate. 2003 Jul. 1; 56 (2):150-61.
29. Wiegel T: Welchen Stellenwert hat die Strahientherapie in der Therapie des Prostatakarzinoms? Urologe B 1998; 38 (suppl 1): 58-64.
30. Wozny W, Schroer K, Schwall G, Stegmann W, Dietz K, Rogatsch H, Huebl H, Klocker H, Schrattenholz A, Cahill M A. Quantitative differential radioactive analysis of protein expression in human prostate cancers reveals novel biomarkers. 2006.

---

The invention claimed is:

1. A method for the diagnosis of prostate or colon cancer comprising analyzing a sample for the presence and/or amount of annexin A3 by detecting annexin A3 with an antibody specific for annexin A3 which has essentially no cross-reactivity against other annexins, wherein the antibody is selected from an antibody produced by the hybridoma cell lines tgc 5 ProII6G7(DSM ACC2778), tgc 6 ProIII1G11 (DSM ACC2779), tgc 7 ProVII5C5(DSM ACC2780), tgc 8 ProIII1E1(DSM ACC2781), tgc 13 ProI/5G9, tgc 12 ProIII/4B11, tgc 14 ProVIII/3D7, or an antibody which binds to the same epitopes on annexin A3 as bound by the antibodies produced by said hybridoma cell lines.

2. The method of claim 1, wherein the antibody is a monoclonal antibody.

3. The method of claim 1, wherein the antibody specifically binds to the N-terminus of annexin A3.

4. The method of claim 1, wherein the antibody specifically binds to an epitope on annexin A3 comprised within a sequence selected from

| i   | VRDYPDFSPSVD;            | (SEQ ID NO: 1) |
| --- | ------------------------ | -------------- |
| ii  | MLISILTERSNA;            | (SEQ ID NO: 2) |
| iii | GDFRKALLTLADGRRDESLKVDEHLAKQ; | (SEQ ID NO: 3) |
| iv  | KLTFDEYRNISQKDIVDSIKGELSG;    | (SEQ ID NO: 4) |
| v   | IMVSRSEIDLLDIRTEF;       | (SEQ ID NO: 5) |
| vi  | YSAIKSDTSGDYEITLL.       | (SEQ ID NO: 6) |

5. The method of claim 1, wherein the antibody carries a labeling group.

6. The method of claim 1, which is a non-invasive procedure.

7. The method of claim 6 wherein the sample is a urine sample.

8. The method of claim 6 wherein the sample is a faeces sample.

9. The method of claim 1, which is a histochemical procedure.

10. The method of claim 9 wherein the sample is a tissue sample.

11. The method of claim 1, wherein the presence and/or amount of extracellular annexin A3 and/or the presence and/or amount of intracellular annexin A3 is determined.

12. The method of claim 1, wherein at least one further marker is determined.

13. The method of claim 12 wherein the further marker is prostate-specific antigen (PSA) and/or prostate specific membrane antigen (PSMA).

14. The method of claim 1, wherein the diagnosis includes a determination of the disease stage.

15. The method of claim 14 wherein at least a differentiation between a precancerous and a cancerous stage is carried out.

16. The method of claim 3, wherein the antibody is directed to an epitope in the region of amino acids 1-16 of human annexin A3.

17. The method of claim 7, wherein the urine sample is an exprimate urine sample.

18. The method of claim 10, wherein the tissue sample is a biopsy.

* * * * *